(12) United States Patent
Bichsel et al.

(10) Patent No.: US 7,311,688 B2
(45) Date of Patent: *Dec. 25, 2007

(54) PERSONAL VAGINAL CLEANING DEVICE

(76) Inventors: John Bichsel, P.O. Box 1456, Largo, FL (US) 33779; Catherine Montgomery, P.O. Box 975, Indian Rocks Beach, FL (US) 33785

( * ) Notice: Subject to any disclaimer, the term of this patent is extended or adjusted under 35 U.S.C. 154(b) by 303 days.

This patent is subject to a terminal disclaimer.

(21) Appl. No.: 10/979,956

(22) Filed: Nov. 3, 2004

(65) Prior Publication Data

US 2006/0069342 A1   Mar. 30, 2006

Related U.S. Application Data

(63) Continuation-in-part of application No. 10/952,621, filed on Sep. 28, 2004, now Pat. No. 7,238,174, and a continuation-in-part of application No. 10/953,909, filed on Sep. 29, 2004, now Pat. No. 7,112,184.

(51) Int. Cl.
*A61M 35/00* (2006.01)

(52) U.S. Cl. .................. 604/2; 604/15; 604/385.17; 604/904

(58) Field of Classification Search ............... 604/1, 604/2, 11–15, 385.17
See application file for complete search history.

(56) References Cited

U.S. PATENT DOCUMENTS

| | | |
|---|---|---|
| 3,724,463 A | 4/1973 | Vail |
| 4,772,274 A | 9/1988 | Lukacs |
| 5,045,058 A | 9/1991 | Demetrakopoulos |
| 5,152,742 A | 10/1992 | Simpson |
| 5,401,240 A | 3/1995 | Yang |

*Primary Examiner*—Tatyana Zalukaeva
*Assistant Examiner*—Melanie J. Hand
(74) *Attorney, Agent, or Firm*—Melvin K. Silverman; Yi Li; Menina Cohen

(57) ABSTRACT

A vaginal cleaning device includes an elongated applicator including an axial support post having a front end and a rear end, a head with a rear surface connected to the front end of the axial support post; a circular disk disposed around the rear end of the axial support post; and a flexible absorbent material disposed around the axial support post between the head and the circular disk. The device has an elongated handle with a front end connected to the rear end of the elongated applicator, a hollow tube with a front open end and a rear open end, disposed around the elongated applicator, and a removable lid on the front open end of the hollow tube. Also disclosed is a method of using the personal vaginal cleaning device.

18 Claims, 2 Drawing Sheets

PERSONAL VAGINAL CLEANING DEVICE

CROSS REFERENCE TO RELATED APPLICATION

This application is a continuation-in-part of patent application Ser. No. 10/952,621, filed on Sep. 28, 2004, now U.S. Pat. No. 7,238,174 and patent application Ser. No. 10/953,909, filed on Sep. 29, 2004 now U.S. Pat. No. 7,112,184. All prior applications are herein incorporated by reference in their entirety.

FIELD OF THE INVENTION

The invention pertains to vaginal cleaning and hygiene device.

BACKGROUND OF THE INVENTION

The vagina is a relatively long hollow, tube like structure that extends from the cervix at the outer end of the uterus down to the labia minora. The interior of the vagina is composed of a mucous membrane and an outer, smooth muscle closely attached to it. While glands are present in the vaginal lining itself, vaginal secretions can arise from the glands in the cervical canal of the uterus such as Bartholin's and Skene's glands. Normally such secretions are clean, but occasionally debris in the form of blood or deposition of seminal fluid can accumulate. Accordingly, it is desirable at times to be able to have a convenient disposable applicator to clean and refresh the vaginal canal to add to or treat the vaginal canal with medications, germicides, or deodorants.

U.S. Pat. No. 5,045,058 by Demetrakopoulos cleanses the vagina by providing an apparatus that delivers lather to the vaginal canal. Vaginal cleaning devices have been addressed in the prior art in terms of a swabbing applicator, as may be seen in U.S. Pat. No. 3,724,463 to Vail. Also, other vaginal cleaning devices that have been addressed in the prior art include a syringe apparatus as may be seen in U.S. Pat. No. 4,772,274 to Lukacs and U.S. Pat. No. 5,401,240 to Yang. U.S. Pat. No. 5,152,742 to Simpson is a swab apparatus for topical use. However, these devices do not satisfactorily consider all issues of size, convenience, portability, simplicity of construction, and effectiveness that are addressed herein.

SUMMARY

The present invention is directed to a personal vaginal cleaning device, which comprises an elongated applicator, an elongated handle, a hollow tube, and a lid. The elongated applicator comprises an axial support post having a front end and a rear end; a head with a rear surface connected to the front end of the axial support post; and a circular disk disposed at the rear end of the axial support post; and a flexible absorbent material disposed around the axial support post between the head and the circular disk. The elongated handle has a front end connected to a rear end of the elongated applicator. The hollow tube has a front open end and a rear open end; the hollow tube being disposed around the elongated applicator. The removable lid on the front end of the hollow tube is for covering the front open end prior to use.

In a further embodiment, the present invention is directed to a method of using the vaginal cleaning device of the present invention. The method includes the steps of providing a personal vaginal cleaning device as described above; opening the lid, and adding a fluid through the front open end of the hollow tube; and allowing the fluid to enter into the applicator to wet the flexible absorbent material; pushing the applicator forward while holding the hollow tube to push the applicator out of the hollow tube into the vagina; removing the hollow tube in a backward direction along the handle; moving the applicator inside the vagina using the handle to clean the vagina; and removing the applicator out from the vagina.

It is an object of the present invention to provide a vaginal cleaning device having functions of cleaning, deodorizing, and medicating the vaginal canal.

Another object is to provide a portable, efficient and effective means to cleanse the vaginal canal prior to or after sexual intercourse.

It is a yet further object to provide a vaginal cleaning device that is more effective than prior art solutions of lathering or scrubbing, and more convenient to use then syringe-like devices.

The above and yet other objects and advantages of the present invention become apparent from the hereinafter set forth Brief Description of the Drawings, Detailed Description of the Invention, and Claims appended herewith.

DETAILED DESCRIPTION OF THE INVENTION

Figure 1:
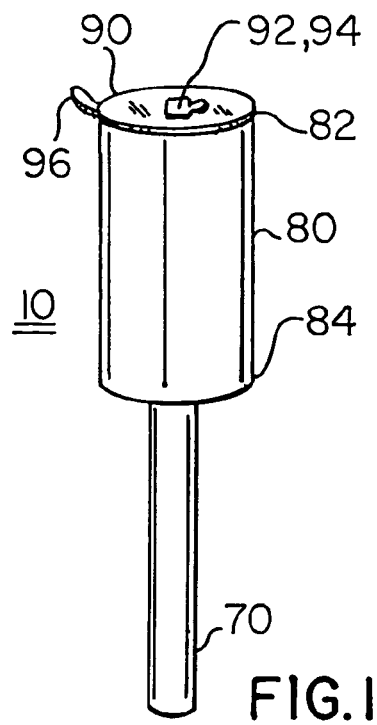
FIG. 1 is a perspective front view of the personal vaginal cleaning device of the present invention.

In one embodiment of the present invention provides a personal vaginal cleaning device, as shown in FIGS. 1 thru 4. The vaginal cleaning device 10 comprises an elongated applicator 20, an elongated handle 70, a hollow tube 80, and a lid 90.

The elongated applicator 20 comprises an axial support post 30 having a front end 32 and an opposing rear end 34 with a head 40 with a rear surface 42 connected to the front end 32 and a circular disk 50 disposed around the rear end 34; and a flexible absorbent material 60 disposed around the axial support post 30 between the head 40 and the circular disk 50. The elongated handle means 70 is connected to the rear end 34 of the axial support post 30. Preferably, the handle means 70 is an integrally dependent from the axial support post 30.

Figure 2:
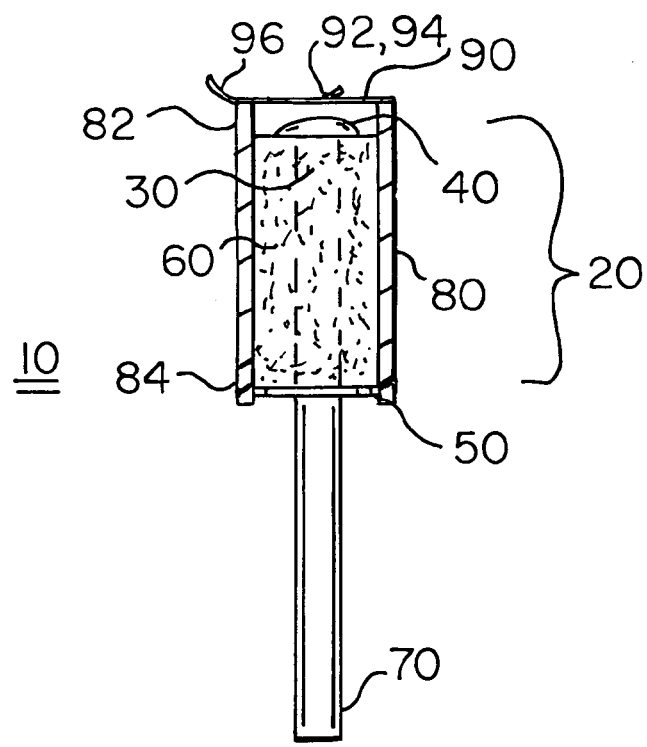
FIG. 2 is a cross sectional view of the personal vaginal cleaning device

As shown in FIG. 2, the elongated applicator 20 is housed within the hollow tube 80. The hollow tube 80 has a front open end 82 and a rear open end 84, and the hollow tube 80 is disposed around the elongated applicator 20.

The head 40 has a semi-spherical front surface for comfortable delivery of the elongated applicator 20 into the vagina of a user. The rear surface 42 of the head 40 is substantially planar.

Figure 3:
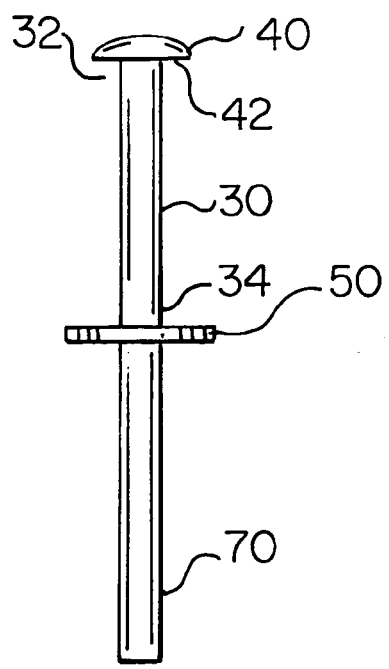
FIG. 3 is a partial perspective front view the personal vaginal cleaning device of FIG. 2, without the flexible absorbent material, and the hollow tube.
Figure 3A:
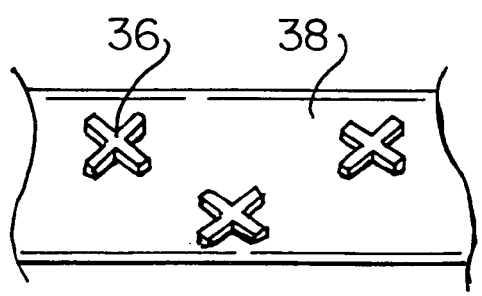
FIG. 3a is an enlarged view of the retention means on the external surface of the axial support post of the device shown in FIG. 3.

The head 40 and the circular disk 50 retain the flexible absorbent material 60 in position and prevent dislocation of the flexible absorbent material 60 during use. Preferably, the lengths of the axial support post 30 and the flexible absorbent material are from about 2.0 to about 3.0 inches. The axial support post 20 further comprises retention means 36. As shown in FIG. 3A, the retention means 36 are a plurality of protruding short rims arranged in a shape of cross 36. However, it should be understood that other shapes and geometries can also be used for the retention means. The retention means 36 are disposed around the surface 38 of the axial support post 30, which further assists to hold the flexible absorbent material 60 in place during use.

Preferably, the inner diameter of the hollow tube 80 is substantially the same to the outer diameter of the circular disk 50 therefore, forming a fluid tight seal at the interface. The outer diameter of the circular disk 50 is larger than that of the head 40. The outer diameter of the head 40 is from about ⅛ to ⅜ inches smaller than the outer diameter of the flexible absorbent material 60, or the inner diameter of the hollow tube 80. As such, when water is added, water can wet the flexible absorbent material 60 without being hindered by the head 40.

Preferably, the flexible absorbent material 60 is porous, such as a sponge material, or ribbed cotton. More preferably, a FDA approved material, such as a sponge made of hydrophilic polyurethane foam, is used. The porous surface of the sponge helps to gently scrub the interior of the vagina, and enhances the effectiveness of cleaning. In one embodiment, the flexible absorbent material 60 has a substantially same outer diameter as that of the circular disk 50, as shown in FIG. 2. Alternatively, the flexible absorbent material 60 can also be expandable, which expands in width upon being released from the hollow tube 80.

The axial support post, head and retention means can be made of a low density polyethylene, preferably, FDA approved material such as USP Class 6B1-ISO10993. Moreover, the axial support post, head, and retention means can also be made of other FDA approved moldable plastic materials.

Figure 4:
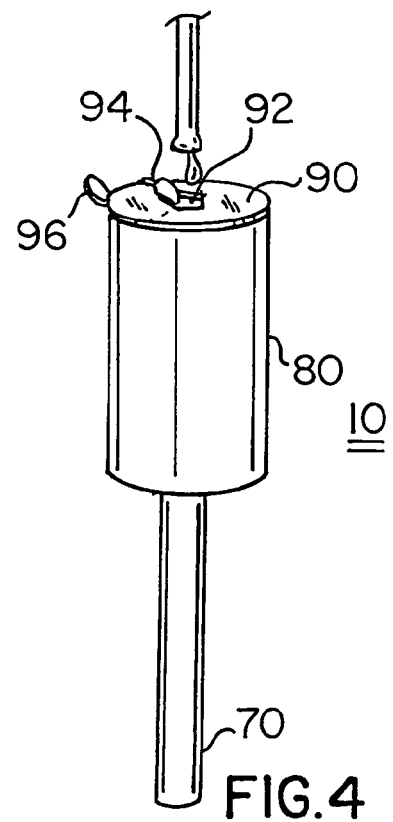
FIG. 4 is an illustrative view of the use of the personal vaginal cleaning device of FIG. 1, wherein a fluid is added into the hollow tube through the sealable opening in the lid of the personal vaginal cleaning device of FIG. 1.

As shown in FIG. 1, the personal vaginal cleaning device 10 has a lid 90 attached to the front open end 82 of the hollow tube 80 for covering the front open end 82 prior to use. Optionally, the lid has a sealable opening 92 located about the center of the lid. The sealable opening 92 is sealed by a sealing material 94. As shown in FIG. 4, the sealable opening 92 is opened to place fluid inside the hollow tube 80 without having to pull the entire lid 90 back. The lid also has a pulling means 96, which may be a tab, to assist the user to easily pull back the lid.

The hollow tube 80 and lid 90 are made of a low density polyethylene, preferably, FDA approved material such as USP Class 6B1-ISO10993. Moreover, the hollow tube 80 and lid 90 can also be made of other FDA approved moldable plastic materials. The sealing material 94 can be made of a foil material similar to the foil used to seal the opening of a drug bottle. The sealing material 94 can also be made of a plastic film, preferably FDA approved material.

The hollow tube 80 can have an inner liquid resistant lining to prevent deformity of the tube once a fluid has been added in.

The vaginal cleaning device 10 can further comprise a pharmaceutically acceptable cleaning agent in the flexible absorbent material 60. The cleaning agent located in the flexible absorbent material 60 can be moistened with water before insertion. The cleaning agent further assists the cleaning.

When in use, the user opens the sealable opening 92, adds water or other suitable fluids through the seatable opening 92 into the hollow tube 80, which allows the water to enter into the tube to wet the flexible absorbent material 60. Since the vaginal cleaning device 10 has an inner diameter of the hollow tube 80 substantially the same as the outer diameter of the circular disk 50 to form a fluid tight seal, the water is maintained inside the elongated applicator 20 prior to inserting the cleaning device.

Figure 5:
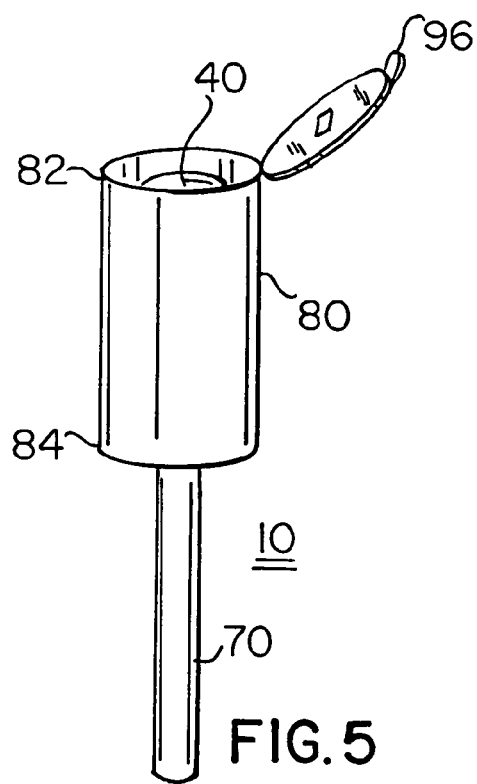
FIG. 5 is an illustrative view wherein the lid is pulled open.

The user opens the lid 90, by pulling on the pulling means 96 and removes and discards the lid as shown in FIG. 5. The user then inserts the front open end 82 of the hollow tube 80 of the vaginal cleaning device 10 into the vaginal canal, and then pushes the elongated applicator 20 forward while holding the hollow tube 80 to push the elongated applicator 20 out of the hollow tube 80 into the vagina. The hollow tube 80 is then removed in a backward direction along the elongate handle 70. The user can move the elongated applicator 20 inside the vagina using the elongate handle 70 to clean the vagina. By moving the elongated applicator 20 the user can rotate the applicator, move forward and backward along the vagina, or combination of both. After cleaning, the user removes the elongated applicator 20 out from the vagina.

Figure 6:
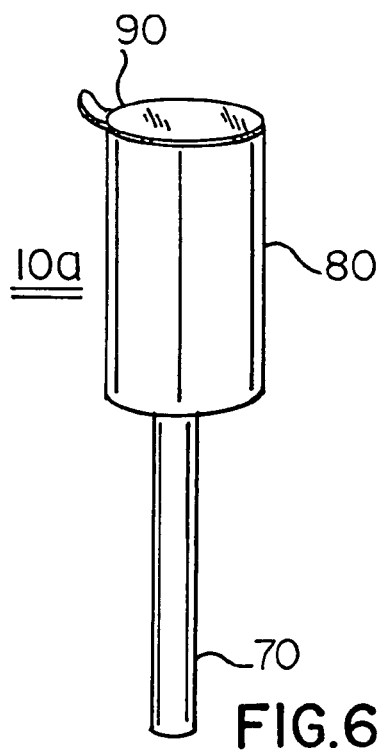
FIG. 6 is a perspective front view of a further embodiment of the personal vaginal cleaning device.

In an alternative embodiment as shown in FIG. 6, the personal vaginal cleaning device 10a has no sealable opening 92 on the lid 90. Using the personal vaginal cleaning device 10a, the user can remove the lid 90, and add water or other fluid directly into the hollow tube 80 to wet the flexible absorbent material 60.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

We claim:

1. A vaginal cleaning device, comprising:
   (a) an elongated applicator comprising an axial support post having a front end and a rear end; a head with a rear surface connected to said front end of said axial support post; and a circular disk disposed around said rear end of said axial support post; and a flexible absorbent material disposed around said axial support post between said head and said circular disk;
   (b) an elongated handle having a front end connected to said rear end of said elongated applicator;
   (c) a hollow tube having a front open end and a rear open end; said hollow tube being disposed around said elongated applicator; and
   (d) a removable lid attached to said front open end of said hollow tube for covering said front open end prior to use.

2. The vaginal cleaning device as recited in claim 1, wherein an outer diameter of said head is smaller than outer diameters of said flexible absorbent material disposed around said axial support post and of said circular disk.

3. The vaginal cleaning device as recited in claim 2, wherein an inner diameter of said hollow tube is substantially same as said outer diameter of said circular disk.

4. The vaginal cleaning device as recited in claim 3, wherein said lid has a sealable opening for introducing a fluid to said elongated applicator through said sealable opening.

5. The vaginal cleaning device as recited in claim 4, where in said lid has a sealing material for sealing said sealable opening and a pulling means for assisting opening of said lid.

6. The vaginal cleaning device as recited in claim 1, wherein said axial support post has retention means on an external surface thereof, for retaining said flexible absorbent material in position.

7. The vaginal cleaning device as recited in claim 5, wherein said retention means is a plurality of protruding rims positioned around said axial support post.

8. The vaginal cleaning device as recited in claim 1, wherein said flexible absorbent material is a sponge made of hydrophilic polyurethane foam.

9. The vaginal cleaning device as recited in claim 1, wherein said flexible absorbent material is ribbed cotton.

10. The vaginal cleaning device as recited in claim 1, wherein said flexible absorbent material is expandable upon releasing from said hollow tube.

11. A method of cleaning vagina comprising the steps of:
(a) providing a cleaning device which comprises:
(i) an elongated applicator comprising an axial support post having a front end and a rear end; a head with a rear surface connected to said front end of said axial support post; and a circular disk disposed around said rear end of said axial support post; and a flexible absorbent material disposed around said axial support post between said head and said circular disk;
(ii) an elongated handle having a front end connected to said rear end of said elongated applicator;
(iii) a hollow tube having a front open end and a rear open end; said hollow tube being disposed around said elongated applicator; and
(iv) a removable lid attached to said front open end of said hollow tube for covering said front open end prior to use;
(b) opening said lid, and adding a fluid through said front open end of said hollow tube, and allowing said fluid to enter into said applicator to wet said flexible absorbent material;
(c) removing said lid and inserting said hollow tube into vagina then pushing said applicator forward while holding said hollow tube to push said applicator out of said hollow tube into the vagina of a user;
(d) removing said hollow tube in a backward direction along said handle;
(e) moving said applicator inside the vagina using said handle to clean the vagina; and
(f) removing said applicator out from the vagina.

12. The method of cleaning vagina as recited in claim 11, wherein an outer diameter of said head is smaller than outer diameters of said flexible absorbent material disposed around said axial support post and of said circular disk, to allow said fluid to enter into said flexible absorbent material.

13. The method of cleaning vagina as recited in claim 11, wherein an inner diameter of said hollow tube is substantially same as said outer diameter of said circular disk to retain water inside said applicator prior to inserting said cleaning device.

14. The method of cleaning vagina as recited in claim 11, wherein said moving said applicator in step (e) includes rotating said applicator, moving forward and backward along the vagina, or combination thereof.

15. A method of cleaning vagina comprising the steps of:
(a) providing a cleaning device which comprises:
(i) an elongated applicator comprising an axial support post having a front end and a rear end; a head with a rear surface connected to said front end of said axial support post; and a circular disk disposed around said rear end of said axial support post; and a flexible absorbent material disposed around said axial support post between said head and said circular disk;
(ii) an elongated handle having a front end connected to said rear end of said elongated applicator;
(iii) a hollow tube having a front open end and a rear open end; said hollow tube being disposed around said elongated applicator; and
(iv) a removable lid attached to said front open end of said hollow tube for covering said front open end prior to use, said lid having a sealable opening;
(b) opening said sealable opening of said lid, and adding said fluid through said sealable opening, and allowing said fluid to enter into said applicator to wet said flexible absorbent material;
(c) removing said lid and inserting said hollow tube into vagina then pushing said applicator forward while holding said hollow tube to push said applicator out of said hollow tube into the vagina of a user;
(d) removing said hollow tube in a backward direction along said handle;
(e) moving said applicator inside the vagina using said handle to clean the vagina; and
(f) removing said applicator out from the vagina.

16. The method of cleaning vagina as recited in claim 15, wherein an outer diameter of said head is smaller than outer diameters of said flexible absorbent material disposed around said axial support post and of said circular disk, to allow said fluid to enter into said flexible absorbent material.

17. The method of cleaning vagina as recited in claim 15, wherein an inner diameter of said hollow tube is substantially same as said outer diameter of said circular disk to retain water inside said applicator prior to inserting said cleaning device.

18. The method of cleaning vagina as recited in claim 15, wherein said moving said applicator in step (e) includes rotating said applicator, moving forward and backward along the vagina, or combination thereof.

* * * * *